United States Patent [19]

Timmer et al.

[11] Patent Number: 5,248,787
[45] Date of Patent: Sep. 28, 1993

[54] VOLATILE ORGANIC BARIUM, STRONTIUM AND CALCIUM COMPOUNDS

[75] Inventors: Klaas Timmer, Bildzigt; Carolus I. M. A. Spee, Klompenmaker; Adrianus Mackor, Mariaplaats; Harmen A. Meinema, Landweg, all of Netherlands

[73] Assignee: Nederlandse Organisatie voor Toegepast Natuurwetenschappelijk Onderzoek - TNO, The Hague, Netherlands

[21] Appl. No.: 533,539

[22] Filed: Jun. 5, 1990

[30] Foreign Application Priority Data

Jun. 14, 1989 [NL] Netherlands ............. 8901507

[51] Int. Cl.$^5$ ............. C07F 3/00; C07F 304; C07C 49/12
[52] U.S. Cl. ............. 549/206; 568/412; 568/613; 568/672; 568/678; 568/679
[58] Field of Search ............. 549/347, 206; 568/412, 568/613, 672, 678, 679

[56] References Cited

FOREIGN PATENT DOCUMENTS 0405634 1/1991 European Pat. Off. .

*Primary Examiner*—C. Warren Ivy
*Assistant Examiner*—A. A. Owens
*Attorney, Agent, or Firm*—Rosen, Dainow & Jacobs

[57] ABSTRACT

Volatile organic barium, strontium and calcium compounds, which consist of the complex of a barium-, strontium- or calcium-$\beta$ diketonate and one or more coordinating ligands, characterized in that at least one coordinating ligand of the barium or strontium compound is formed by a neutral oxygen or a neutral nitrogen donor ligand, or one of the coordinating ligands of the calcium compound is formed by a neutral oxygen donor ligand.

6 Claims, No Drawings

VOLATILE ORGANIC BARIUM, STRONTIUM AND CALCIUM COMPOUNDS

BACKGROUND OF THE INVENTION

The invention relates to new volatile organic barium, strontium and calcium compounds.

Volatile organic barium, strontium and calcium compounds are known.

P. H. Dickinson, A. Sanjurjo, T. H. Geballe, D. Hildenbrandt, G. Graig, M. Zisk, J. Collman, S. A. Banning and R. E. Sievers for instance, in J.Appl.Phys.1989, 66, 444, describe the use of the 2,2,6,6-tetramethyl-3,5-heptanedione (thd) compound of—among others—Ba, that is {Ba(thd)$_2$}, as precursor for so-called chemical vapor deposition (CVD) processes. This compound has been found to dissociate partially during evaporation, because of which its concentration in the vapor phase diminishes as a function of time, at a constant temperature of the source, in this case Ba(thd)$_2$ in the solid phase.

Other volatile barium-, strontium- and calcium-$\beta$-diketonates are also known, for instance from the work of J. E. Schwarberg, R. E. Sievers and R. W. Moshier, in Anal.Chem. 1970, 42, 1828. It has been found, however, that when these compounds are heated to 200° C. and higher temperatures, which is necessary to bring them from the solid phase into the gas phase, a rapid decomposition occurs.

Barium-, strontium- and calcium-$\beta$-diketonates are described—among others—by D. E. Fenton in "Comprehensive Coordination Chemistry", Editor in Chief G. Wilkinson, in Volume 3, Chapter 23.4.1., pages 25 and on.

It has now been found that the problems encountered with known volatile compounds so far can be overcome by applying certain combinations of barium-, strontium- and calcium-$\beta$-diketonates and coordinating ligands.

DETAILED DESCRIPTION OF THE INVENTION

The invention relates to new volatile organic barium, strontium and calcium compounds, which consist of the complex of a barium-, strontium- or calcium-$\beta$-diketonate and one or more coordinating ligands, characterized in that at least one coordinating ligand of the barium or strontium compound is formed by a neutral oxygen or a neutral nitrogen donor ligand or one of the coordinating ligands of the calcium compound is formed by a neutral oxygen donor ligand.

The general structure formula of a compound according to the invention is given on the formula sheet. In this structure formula, M represents a barium, strontium or calcium ion with valence 2, R' and R" represent the side chains of the diketonate, L represents the neutral oxygen or neutral nitrogen donor coordinating ligand and m the number of coordinating ligands.

Complexes of barium-, strontium- and calcium-$\beta$-diketonates according to the invention possess a much higher volatility and thermal stability than similar barium-, strontium- and calcium-$\beta$-diketonates lacking the complexing ligand.

As mentioned above, the $\beta$-diketonates of barium, strontium and calcium, when lacking a complexing ligand, are thermally instable. With barium-, strontium- or calcium-$\beta$-diketonate ligand complexes according to the invention, conditions can be attained under which, for instance in a CVD process, during a longer period of time (several days), a constant mass transport of calcium, strontium or barium compounds per unit of time can be maintained.

Appropriate neutral oxygen donor ligands in practical examples of compounds according to the invention are:

acyclic ethers with the general formula ROR', with R and R' representing a $C_1$-$C_8$ group;

cyclic ethers, $(CRR')_nO$, $\{(CRR')_nO\}_m$, with R,R'=H, (substituted) alkyl, n,m=1–6, for instance crown ethers like 18-crown-6 and other;

glycol ethers, R'O—$(CHRCH_2O)_n$—H, e.g. tetraethyleneglycol monomethyl ether and R'O—$(CHRCH_2O)_n$—R", in which R=H,Me and R',R"=(substituted) alkyl, n=1–6, for instance R=H, R'=R"=Me, glyme (n=1; dimethoxyethane,DME), diglyme (n=2), triglyme (n=3), tetraglyme (n=4), hexaglyme (n=6) and other;

polyethers, $RO[(CR'R'')_nO]_mH$ and $RO[(CR'R'')_nO]_mR'$ in which R=(substituted)alkyl and R',R"=H, (substituted)alkyl, n=1–4, m=1–6;

alcohols, ROH, $HO(CR'R'')_nOH$, $HO\{(CR'R'')_nO\}_mH$, with R=(substituted) alkyl and R',R"=H, (substituted)alkyl, n,m=1–6;

ketones, R—C(O)—R', R—C(O)$(CR''R''')_n$C(O)—R', with R and R' representing a $C_1$-$C_8$ group and R",R'''=H, (substituted)alkyl, n≧2;

aldehydes, RC(O)H, with R=$C_1$-$C_8$ group;

anhydrides, $\{RC(O)\}_2O$, with R=$C_1$-$C_8$ group;

amides, RR'NC(O)H, with R and R' representing a $C_1$-$C_8$ group, for instance dimethylformamide (DMF) and other;

sulfoxides, RS(O)R', with R and R' representing a $C_1$-$C_8$ group, for instance dimethylsulfoxide (DMSO) and other;

sulfones, $RS(O)_2R'$, with R and R' representing a $C_1$-$C_8$ group;

cyclic sulfones, $(CRR')_nS(O)_2$, with R,R'=H, (substituted)alkyl, for instance $\{(CH_2)_4SO_2\}$ (sulfolane) and other.

Appropriate neutral nitrogen donor ligands are:

nitriles, RCN, with R=$C_1$-$C_8$ group;

dinitriles, $NC(CRR')_nCN$, with R and R'=H and/or $C_1$-$C_8$ group(s), n≧1;

amines, RR'R"N, with R, R', R"=H and/or $C_1$-$C_8$ group(s);

di- and polyamines, for instance tetramethylethylenediamine (TMED) and other;

pyridines, $C_5R_nH_{5-n}N$, with R=$C_1$-$C_8$ group, n=0–5;

dipyridines, for instance 2,2'-dipyridine and other;

phenanthrolines;

imines, RCH=NR', with R and R'=$C_1$-$C_8$ group;

diimines, R—N=CH—CH=N—R', with R and R'=$C_1$-$C_8$ group.

The synthesis of the barium-, strontium- and calcium-$\beta$-diketonate ligand complexes proceeds by a reaction of the required amount of complexing ligand with the appropriate barium-, strontium- or calcium-$\beta$-diketonate in an inert solvent such as toluene or pentane.

It has been found that the stability of the compounds is markedly improved when at least one of the side chains R' and R" of the $\beta$-diketonate contains a fluorine-substituted alkyl and/or aryl group.

In a preferred realisation of the invention, at least one of the side chains R' and R" consists of the alkyl groups $CF_3$ and/or n-$C_3F_7$.

With compounds according to this preferred realisation, very stable and volatile barium-, strontium- and calcium-β-diketonate ligand complexes at elevated temperatures and/or lowered pressures are formed.

The following structure formulas give a number of representative examples of barium, strontium and calcium compounds according to the invention:

1. Ba{$CF_3C(O)CHC(O)CF_3$}$_2$ . 2{$CH_3OCH_2CH_2OCH_3$}.
2. Ba{$CF_3C(O)CHC(O)CF_3$}$_2$ . 3{$(CH_3)_2NC(O)H$}.
3. Ba{$CF_3C(O)CHC(O)CF_3$}$_2$ . 2{$(CH_3)_2NCH_2CH_2N(CH_3)_2$}.
4. Ba{$CF_3C(O)CHC(O)CF_3$}$_2$ . 2{$CH_3O(CH_2CH_2O)_2CH_3$}.
5. Ba{$CF_3C(O)CHC(O)CF_3$}$_2$ . {$CH_3O(CH_2CH_2O)_3CH_3$}.
6. Ba{$CF_3C(O)CHC(O)CF_3$}$_2$ . {$CH_3O(CH_2CH_2O)_4CH_3$}.
7. Ba{$CF_3C(O)CHC(O)CF_3$}$_2$ . {$(CH_2CH_2O)_6$}.
8. Ba{$CF_3C(O)CHC(O)CF_3$}$_2$ . {$CH_3O(CH_2CH_2O)_6CH_3$}.
9. Ba{$CF_3C(O)CHC(O)CF_3$}$_2$ . 6{$CH_3S(O)CH_3$}.
10. Ba{$CF_3C(O)CHC(O)CF_3$}$_2$ . 9{$(CH_2)_4SO_2$}.
11. Ba{$CF_3C(O)CHC(O)CF_3$}$_2$ . {o-(2-$C_5H_4N)C_5H_4N$}.
12. Ba{$CF_3C(O)CHC(O)CF_3$}$_2$ . {$HO(CH_2CH_2O)_4CH_3$}.
13. Ba{$CF_3C(O)CHC(O)CH_3$}$_2$ . {$CH_3O(CH_2CH_2O)_4CH_3$}.
14. Ba{$CF_3C(O)CHC(O)CH_3$}$_2$ . {$(CH_2CH_2O)_6$}.
15. Ba{$CF_3CF_2CF_2C(O)CHC(O)C(CH_3)_3$}$_2$ . {$CH_3O(CH_2CH_2O)_4CH_3$}.
16. Ba{$CF_3CF_2CF_2C(O)CHC(O)C(CH_3)_3$}$_2$ . {$CH_3O(CH_2CH_2O)_6CH_3$}.
17. Sr{$CF_3C(O)CHC(O)CF_3$}$_2$ . 2{$CH_3OCH_2CH_2OCH_3$}.
18. Sr{$CF_3C(O)CHC(O)CF_3$}$_2$ . {$CH_3O(CH_2CH_2O)_4CH_3$}.
19. Ca{$CF_3C(O)CHC(O)CF_3$}$_2$ . 2{$CH_3OCH_2CH_2OCH_3$}.
20. Ca{$CF_3C(O)CHC(O)CF_3$}$_2$ . {$CH_3O(CH_2CH_2O)_3CH_3$}.
21. Ca{$CF_3C(O)CHC(O)CH_3$}$_2$ . {$CH_3O(CH_2CH_2O)_3CH_3$}.

The volatility of these compounds and the corresponding barium-, strontium- and calcium-β-diketonates are shown in Table 1. As the table shows, these compounds sublime at reduced pressure (0.01–0.5 mm Hg) at temperatures between 85° C. and 180° C. This means that they are especially appropriate as precursor for so-called metal-organic chemical vapor deposition (MO-CVD) of materials containing the corresponding metals.

The invention also deals with a method for the preparation of layered materials which contain barium, strontium or calcium oxides or fluorides, by means of a deposition technique.

Such a method is known, for instance from the publication of Dickinson et al., mentioned above.

With the known methods, especially MO-CVD, one encounters problems with the deposition of some barium, strontium or calcium containing layered structures, because of the low volatility and the rapid decomposition of the precursor from which the deposition should take place.

The invention aims at eliminating those problems and thereto provides a method, characterized in that with the deposition technique one starts with volatile organic barium, strontium or calcium compounds according to the invention described above, corresponding to the desired barium, strontium or calcium oxides or fluorides.

Without excluding other deposition techniques such as dip coating, (plasma)-spray-pyrolysis and spin coating, the compounds and procedures according to the invention are particularly appropriate when applied with MO-CVD.

By using volatile and stable compounds according to the invention, in a MO-CVD process, barium, strontium and/or calcium oxide-containing materials can be prepared easily with this technique. The applicability of MO-CVD for such materials is of importance especially for preparation of and research on recently discovered mixed metal oxides, superconductive at relative high temperatures.

In an alternative realisation of the method according to the invention, the organic barium, strontium and calcium compounds are formed during the MO-CVD process by adding a coordinating ligand in liquid or vapor phase to the barium-, strontium- or calcium-β-diketonate. Also with this method an increased and more constant mass transport of the barium-, strontium- and calcium-β-diketonate can be obtained.

IMPLEMENTATION EXAMPLES

The following examples illustrate the methods and chemical preparation of the compounds of this invention and as such are not to be constructed as limiting the scope thereof. All reactions are carried out in a dry atmosphere and at room temperature unless otherwise stated.

Example 1

Ba{$CF_3C(O)CHC(O)CF_3$}$_2$ . 2{$CH_3OCH_2CH_2OCH_3$}. (1)

0.4 ml of $CH_3OCH_2CH_2OCH_3$ (glyme, DME) is added to a stirred suspension of 0.54 g (0.98 mmol) of Ba{$CF_3C(O)CHC(O)CF_3$}$_2$ in 15 ml of toluene. Stirring is continued for 0.5 h. The slightly turbid reaction mixture is filtered and the clear filtrate is evaporated to dryness under reduced pressure at 30° C. The beige coloured solid product thus obtained is dried in vacuo at room temperature for 4 h.

Yield: 0.6 g of 1 (84.5%).
Melting point: 45°–47° C.
$^1$H NMR in $C_6D_6$: δ($CH_3$) 3.01 ppm (s) δ($CH_2CH_2$) 2.87 ppm (s) δ(CH) 6.18 ppm (s).
Elemental analysis: found (calculated) (%) C 29.14 (29.54); H 3.00 (3.01); F 30.16 (31.18).

Example 2

Ba{$CF_3C(O)CHC(O)CF_3$}$_2$ . 3{$(CH_3)_2NC(O)H$}. (2)

0.58 g (7.98 mmol) of $(CH_3)_2NC(O)H$ (DMF) is added dropwise to a stirred suspension of 0.55 g (0.99 mmol) of Ba{$CF_3C(O)CHC(O)CF_3$}$_2$ in 15 ml of toluene. Stirring is continued for about 0.5 h. The clear reaction mixture is evaporated to dryness under reduced pressure at 30° C. The residue is dissolved in 20 ml of toluene and the clear solution is evaporated to dryness at reduced pressure at 30° C. The beige coloured residue (a syrup) is dried in vacuo at room temperature for 4 h.

Yield: 0.56 g of 2 (73.6%).
$^1$H NMR in $C_6D_6$: δ($CH_3$) 2.11 and 2.49 ppm (s) δ(CH-DMF) 7.76 ppm (s) δ(CH) 6.09 ppm (s).

Elemental analysis: found (calculated) (%). C 29.40 (29.60); H 2.94 (2.99); N 4.98 (5.45).

Example 3

Ba{CF$_3$C(O)CHC(O)CF$_3$}$_2$ · 2{(CH$_3$)$_2$NCH$_2$CH$_2$N(CH$_3$)$_2$}. (3)

0.36 g (3.12 mmol) of (CH$_3$)$_2$NCH$_2$CH$_2$N(CH$_3$)$_2$ (TMED) is added dropwise to a stirred suspension of 0.43 g (0.78 mmol) of Ba{CF$_3$C(O)CHC(O)CF$_3$}$_2$ in 15 ml of toluene. Stirring is continued for about 0.5 h. The clear reaction mixture is evaporated to dryness under reduced pressure at 30° C. The beige coloured solid residue is dried in vacuo at room temperature for 4 h.

Yield: 0.57 g of 3 (93.4%).
Melting point: 118°–120° C.
$^1$H NMR in C$_6$D$_6$: δ(CH$_3$) 1.94 ppm (s) δ(CH$_2$CH$_2$) 1.84 ppm (s) δ(CH) 6.28 ppm (s).
Elemental analysis: found (calculated) (%) C 33.64 (33.70); H 4.43 (4.34); N 7.02 (7.15).

Example 4

Ba{CF$_3$C(O)CHC(O)CF$_3$}$_2$ · 2{CH$_3$O(CH$_2$CH$_2$O)$_2$CH$_3$}. (4)

0.41 g (3.05 mmol) of CH$_3$O(CH$_2$CH$_2$O)$_2$CH$_3$ (diglyme) is added dropwise to a stirred suspension of 0.84 g (1.52 mmol) of Ba{CF$_3$C(O)CHC(O)CF$_3$}$_2$ in 15 ml of toluene. Stirring is continued for about 1 h. The slightly turbid reaction mixture is filtered and the clear filtrate is evaporated to dryness under reduced pressure at 30° C. The colourless solid residue is dried in vacuo at room temperature for 4 h.

Yield: 1.16 g of 4 (93.6%).
Melting point: 110°–112° C.
$^1$H NMR in C$_6$D$_6$: δ(CH$_3$) 3.06 ppm (s) δ(CH$_2$CH$_2$) 3.14 ppm (m) δ(CH) 6.22 ppm (s).
Elemental analysis: found (calculated) (%) C 32.30 (32.22); H 3.66 (3.66); F 27.92 (27.83).

Example 5

Ba{CF$_3$C(O)CHC(O)CF$_3$}$_2$ · {CH$_3$O(CH$_2$CH$_2$O)$_3$CH$_3$}. (5)

0.24 g (1.36 mmol) of CH$_3$O(CH$_2$CH$_2$O)$_3$CH$_3$ (triglyme) is added dropwise to a stirred suspension of 0.75 g (1.36 mmol) of Ba{CF$_3$C(O)CHC(O)CF$_3$}$_2$ in 20 ml of toluene. Stirring is continued for about 1 h. The almost clear reaction mixture is filtered and the clear filtrate is evaporated to dryness under reduced pressure at 40° C. The colourless solid residue is recrystallized from a mixture of toluene and pentane and then dried in vacuo at room temperature for 4 h.

Yield: 0.51 g of 5 (51.5%).
Melting point: 105°–107° C.
$^1$H NMR in C$_6$D$_6$: δ(CH$_3$) 3.00 ppm (s) δ(CH$_2$CH$_2$) 2.94 ppm (m) δ(CH) 6.20 ppm (s).
Elemental analysis: found (calculated) (%) C 29.67 (29.62); H 3.13 (2.74).

Example 6

Ba{CF$_3$C(O)CHC(O)CF$_3$}$_2$ · {CH$_3$O(CH$_2$CH$_2$O)$_4$CH$_3$}. (6)

0.43 g (1.94 mmol) of CH$_3$O(CH$_2$CH$_2$O)$_4$CH$_3$ (tetraglyme) is added dropwise to a stirred suspension of 1.07 g (1.94 mmol) of Ba{CF$_3$C(O)CHC(O)CF$_3$}$_2$ in 20 ml of toluene. Stirring is continued for about 1 h. The slightly turbid reaction mixture is filtered and the clear filtrate is evaporated to dryness under reduced pressure at 30° C. The colourless solid residue is dried in vacuo at room temperature for 4 h.

Yield: 1.42 g of 6 (94.7%).
Melting point: 145°–147° C.
$^1$H NMR in C$_6$D$_6$: δ(CH$_3$) 3.18 ppm (s) δ(CH$_2$CH$_2$) 2.87 ppm (s) and 3.18 ppm (m) δ(CH) 6.23 ppm (s).
Elemental analysis: found (calculated) (%) C 31.61 (31.03); H 3.36 (3.10).

Example 7

Ba{CF$_3$C(O)CHC(O)CF$_3$}$_2$ · {(CH$_2$CH$_2$O)$_6$}. (7)

A solution of 0.306 g (1.16 mmol) of (CH$_2$CH$_2$O)$_6$ (18-crown-6) in 7 ml of toluene is added dropwise to a stirred suspension of 0.64 g (1.16 mmol) of Ba{CF$_3$C(O)CHC(O)CF$_3$}$_2$ in 15 ml of toluene. Stirring is continued for about 1 h. The slightly turbid reaction mixture is filtered and the clear filtrate is evaporated to dryness under reduced pressure at 30° C. The colourless solid residue is dried in vacuo at room temperature for 4 h.

Yield: 0.88 g of 7 (93.0%).
Melting point: 234°–236° C.
$^1$H NMR in C$_6$D$_6$: δ(CH$_2$CH$_2$) 3.20 ppm (s) δ(CH) 6.23 ppm (s).
Elemental analysis: found (calculated) (%) C 32.45 (32.38); H 3.36 (3.19).

Example 8

Ba{CF$_3$C(O)CHC(O)CF$_3$}$_2$ · {CH$_3$O(CH$_2$CH$_2$O)$_6$CH$_3$}. (8)

2.70 g (8.72 mmol) of CH$_3$O(CH$_2$CH$_2$O)$_6$CH$_3$ (hexaglyme) is added dropwise to a stirred suspension of 4.81 g (8.72 mmol) of Ba{CF$_3$C(O)CHC(O)CF$_3$}$_2$ in 75 ml of toluene. Stirring is continued for about 1 h. The slightly turbid reaction mixture is filtered and the clear filtrate is evaporated to dryness under reduced pressure at 40° C. The off-white solid residue is recrystallized from pentane. The colourless product is then dried in vacuo at 50° C. for 4 h.

Yield: 5.64 g of 8 (75.1%).
Melting point: 70°–72° C.
$^1$H NMR in C$_6$D$_6$: δ(CH$_3$) 3.11 ppm (s) δ(CH$_2$CH$_2$) 3.17, 3.26, 3.32 and 3.40 ppm (m) δ(CH) 6.25 ppm (s).
Elemental analysis: found (calculated) (%) C 33.35 (33.44); H 3.80 (3.72); F 26.25 (26.47).

Example 9

Ba{CF$_3$C(O)CHC(O)CF$_3$}$_2$ · 6{CH$_3$S(O)CH$_3$}. (9)

0.75 g (9.58 mmol) of CH$_3$S(O)CH$_3$ (DMSO) is added to a stirred suspension of 0.66 g (1.20 mmol) of Ba{CF$_3$C(O)CHC(O)CF$_3$}$_2$ in 15 ml of toluene. Stirring is continued for about 1 h. The slightly turbid reaction mixture is filtered and the clear filtrate is evaporated to dryness under reduced pressure at 40° C. The oily residue is washed thrice with 25 ml of pentane. The light yellow product (a syrup) is then dried in vacuo at room temperature for 4 h.

Yield: 1.05 g of 9 (86.1%).
$^1$H NMR in C$_6$D$_6$: δ(CH$_3$) 1.95 ppm (s) δ(CH) 6.28 ppm (s).
Elemental analysis: found (calculated) (%) C 25.88 (25.88); H 3.83 (3.73); S 19.35 (18.88).

Example 10

Ba{CF$_3$C(O)CHC(O)CF$_3$}$_2$ . 9{(CH$_2$)$_4$SO$_2$}. (10)

0.99 g (8.27 mmol) of (CH$_2$)$_4$SO$_2$ (sulfolane) is added to a stirred suspension of 0.57 g (1.03 mmol) of Ba{CF$_3$C(O)CHC(O)CF$_3$}$_2$ in 15 ml of toluene. Stirring is continued for about 1 h. The clear reaction mixture is evaporated to dryness under reduced pressure at 40° C. The oily residue is washed thrice with 25 ml of pentane. The light yellow product (an oil) is then dried in vacuo at room temperature for 4 h.

Yield: 1.53 g of 10 (90.7%).

$^1$H NMR in CD$_3$C(O)CD$_3$: δ(CH$_2$S) 2.76 ppm (m) δ(CH$_2$CH$_2$) 1.90 ppm (m) δ(CH) 5.84 ppm (s).

Elemental analysis: found (calculated) (%) C 33.97 (33.82); H 4.72 (4.53); S 17.72 (17.68).

Example 11

Ba{CF$_3$C(O)CHC(O)CF$_3$}$_2$ . {o-(2—C$_5$H$_4$N)C$_5$H$_4$N}. (11)

0.70 g (4.46 mmol) of o-(2—C$_5$H$_4$N)C$_5$H$_4$N (2,2'-dipyridine) is added to a stirred suspension of 0.82 g (1.49 mmol) of Ba{CF$_3$C(O)CHC(O)CF$_3$}$_2$ in 30 ml of toluene. Stirring is continued for 0.5 h at room temperature and 0.5 h at 55° C. After cooling to room temperature the precipitated colourless product is filtered off and washed with toluene and pentane. The product is then dried in vacuo above KOH for 3 days.

Yield: 0.9 g of 11 (85.7%).

Melting point: 214°–216° C.

$^1$H NMR in CD$_3$C(O)CD$_3$: δ(C$_5$H$_4$) 7.40, 7.93, 8.55 and 8.83 ppm (m) δ(CH) 5.66 ppm (s).

Elemental analysis: found (calculated) (%) C 33.78 (33.93); H 1.52 (1.41); N 3.93 (3.96).

Example 12

Ba{CF$_3$C(O)CHC(O)CF$_3$}$_2$ . {HO(CH$_2$CH$_2$O)$_4$CH$_3$}. (12)

0.35 g (1.67 mmol) of HO(CH$_2$CH$_2$O)$_4$CH$_3$ (tetraethyleneglycol monomethyl ether) is added dropwise to a stirred suspension of 0.92 g (1.67 mmol) of Ba{CF$_3$C(O)CHC(O)CF$_3$}$_2$ in 20 ml of toluene. Stirring is continued for about 1 h. The slightly turbid reaction mixture is filtered and the clear filtrate is evaporated to dryness under reduced pressure at 40° C. The off-white residue is stirred with 20 ml of pentane for 0.5 h and then filtered off. The colourless product is then dried in vacuo at room temperature for 4 h.

Yield: 1.07 g of 12 (84.9%).

Melting point: 144°–146° C.

$^1$H NMR in C$_6$D$_5$CD$_3$: δ(CH$_3$) 3.13 ppm (s) δ(CH$_2$CH$_2$) 2.90–3.22 ppm (m) δ(OH) 2.78 ppm (s;br) δ(CH) 6.19 ppm (s).

Elemental analysis: found (calculated) (%) C 30.04 (30.03); H 2.98 (2.90).

Example 13

Ba{CF$_3$C(O)CHC(O)CH$_3$}$_2$ . {CH$_3$O(CH$_2$CH$_2$O)$_4$CH$_3$}. (13)

0.22 g (1.00 mmol) of CH$_3$O(CH$_2$CH$_2$O)$_4$CH$_3$ (tetraglyme) is added dropwise to a stirred suspension of 0.44 g (1.00 mmol) of Ba{CF$_3$C(O)CHC(O)CH$_3$}$_2$ in 10 ml of toluene. Stirring is continued for about 1 h. The resulting solution is evaporated to dryness under reduced pressure at 40° C. The solid residue is stirred with 20 ml of pentane for 0.5 h and then filtered off. The colourless product is then dried in vacuo at room temperature for 4 h.

Yield: 0.59 g of 13 (89.4%).

Melting point: 140°–142° C.

$^1$H NMR in C$_6$D$_6$: δ(OCH$_3$) 3.30 ppm (s) δ(CH$_2$CH$_2$) 2.98, 3.20 and 3.36 ppm (m) δ(CH$_3$) 1.89 ppm (s) δ(CH) 5.80 ppm (s).

Elemental analysis: found (calculated) (%) C 36.02 (36.07); H 4.58 (4.51).

Example 14

Ba{CF$_3$C(O)CHC(O)CH$_3$}$_2$ . {(CH$_2$CH$_2$O)$_6$}. (14)

0.26 g (1.00 mmol) of (CH$_2$CH$_2$O)$_6$ (18-crown-6) is added to a stirred solution of 0.44 g (1.00 mmol) of Ba{CF$_3$C(O)CHC(O)CH$_3$}$_2$ in a mixture of 15 ml of toluene and 5 ml of ethanol. Stirring is continued for about 1 h. The solution is evaporated to dryness under reduced pressure at 40° C. The solid residue is stirred with 25 ml of pentane for 0.5 h and then filtered off. The off-white product is then dried in vacuo at room temperature for 4 h.

Yield: 0.66 g of 14 (94.0%).

Melting point: 190°–192° C. (dec).

$^1$H NMR in CDCl$_3$: δ(CH$_2$CH$_2$) 3.78 ppm (s) δ(CH$_3$) 1.99 ppm (s) δ(CH) 5.43 ppm (s).

Elemental analysis: found (calculated) (%) C 37.04 (37.32); H 4.53 (4.52).

Example 15

Ba{CF$_3$CF$_2$CF$_2$C(O)CHC(O)C(CH$_3$)$_3$}$_2$ . {CH$_3$O(CH$_2$CH$_2$O)$_4$CH$_3$}. (15)

0.51 g (2.28 mmol) of CH$_3$O(CH$_2$CH$_2$O)$_4$CH$_3$ (tetraglyme) is added dropwise to a stirred solution of 1.70 g (2.28 mmol) of Ba{CF$_3$CF$_2$CF$_2$C(O)CHC(O)C(CH$_3$)$_3$}$_2$ in 60 ml of toluene. Stirring is continued for about 1 h. The solution is evaporated to dryness under reduced pressure at 40° C. The residue is dissolved in 20 ml of pentane and this solution is also evaporated to dryness under reduced presure at 30° C. The off-white residue (a syrup) is cooled to −20° C. upon which the product solidified. The product is then dried in vacuo at room temperature for 4 h.

Yield: 1.94 g of 15 (89.8%).

Melting point: 48°–50° C.

$^1$H NMR in CDCl$_3$: δ(OCH$_3$) 3.33 ppm (s) δ(CH$_2$CH$_2$) 3.46, 3.56, 3.71 and 3.79 ppm (m) δ(t-Bu) 1.11 ppm (s) δ(CH) 5.65 ppm (s).

Elemental analysis: found (calculated) (%) C 38.33 (37.92); H 4.52 (4.42); F 27.48 (28.02).

Example 16

Ba{CF$_3$CF$_2$CF$_2$C(O)CHC(O)C(CH$_3$)$_3$}$_2$ . {CH$_3$O(CH$_2$CH$_2$O)$_6$CH$_3$}. (16)

0.45 g (1.44 mmol) of CH$_3$O(CH$_2$CH$_2$O)$_6$CH$_3$ (hexaglyme) is added dropwise to a stirred suspension of 1.05 g (1.44 mmol) of Ba{CF$_3$CF$_2$CF$_2$C(O)CHC(O)C(CH$_3$)$_3$}$_2$ in 15 ml of pentane. Stirring is continued for 0.5 h. The slightly turbid reaction mixture is filtered and the clear filtrate is evaporated to dryness under reduced pressure at 30° C. The off-white product is then dried in vacuo at room temperature for 4 h.

Yield: 1.43 g of 16 (96.0%).

Melting point: 68°–70° C.

$^1$H NMR in CDCl$_3$: δ(OCH$_3$) 3.31 ppm (s) δ(CH$_2$CH$_2$) 3.49, 3.61, 3.68 and 3.69 ppm (m) δ(t-Bu) 1.11 (s) δ(CH) 5.63 (s).

Elemental analysis: found (calculated) (%) C 39.06 (39.33); H 4.59 (4.82).

Example 17

$Sr\{CF_3C(O)CHC(O)CF_3\}_2 \cdot 2\{CH_3OCH_2CH_2OCH_3\}$. (17)

0.54 ml of $CH_3OCH_2CH_2OCH_3$ (glyme, DME) is added dropwise to a stirred suspension of 0.66 g (1.32 mmol) of $Sr\{CF_3C(O)CHC(O)CF_3\}_2$ in 15 ml of toluene. Stirring is continued for about 0.5 h. The slightly turbid reaction mixture is filtered and the clear filtrate is evaporated to dryness under reduced pressure at 30° C. The colourless solid residue is dried in vacuo at room temperature for 4 h.

Yield: 0.84 g of 17 (94.4%).
Melting point: 80°-82° C.
$^1$H NMR in $C_6D_6$: $\delta(CH_3)$ 3.08 ppm (s) $\delta(CH_2CH_2)$ 2.81 ppm (s) $\delta(CH)$ 6.27 ppm (s).
Elemental analysis: found (calculated) (%) C 31.66 (31.69); H 3.27 (3.32); F 33.51 (33.45).

Example 18

$Sr\{CF_3C(O)CHC(O)CF_3\}_2 \cdot (CH_3O(CH_2CH_2O)_4CH_3$. (18)

4.53 g (20.39 mmol) of $CH_3O(CH_2CH_2O)_4CH_3$ (tetraglyme) is added dropwise to a stirred suspension of 10.23 g (20.39 mmol) of $Sr\{CF_3C(O)CHC(O)CF_3\}_2$ in 160 ml of toluene. Stirring is continued for 1 h. The slightly turbid reaction mixture is filtered and the clear filtrate is evaporated to dryness under reduced pressure at 40° C. The solid residue is stirred with 100 ml of pentane for 0.5 h and then filtered off. The colourless product is then dried in vacuo at room temperature for 4 h.

Yield: 12.91 g of 18 (87.5%).
Melting point: 137°-139° C.
$^1$H NMR in CDCl$_3$: $\delta(CH_3)$ 3.34 ppm (s) $\delta(CH_2CH_2)$ 3.46, 3.57, 3.76 and 3.79 ppm (m) $\delta(CH)$ 5.88 ppm (s).
Elemental analysis: found (calculated) (%) C 33.28 (33.17); H 3.34 (3.32).

Example 19

$Ca\{CF_3C(O)CHC(O)CF_3\}_2 \cdot 2\{CH_3OCH_2CH_2OCH_3\}$. (19)

1.2 ml of $CH_3OCH_2CH_2OCH_3$ (glyme, DME) is added dropwise to a stirred suspension of 1.31 g (2.88 mmol) of $Ca\{CF_3C(O)CHC(O)CF_3\}_2$ in 15 ml of toluene. Stirring is continued for about 0.5 h. The slightly turbid reaction mixture is filtered and the clear filtrate is evaporated to dryness under reduced pressure at 30° C. The colourless solid residue is dried in vacuo at room temperature for 4 h.

Yield: 1.74 g of 19 (95.1%).
Melting point: 80°-82° C.
$^1$H NMR in $C_6D_6$: $\delta(CH_3)$ 3.11 ppm (s) $\delta(CH_2CH_2)$ 2.80 ppm (s) $\delta(CH)$ 6.21 ppm (s).
Elemental analysis: found (calculated) (%) C 33.52 (34.07); H 3.53 (3.47); F 35.36 (35.96).

Example 20

$Ca\{CF_3C(O)CHC(O)CF_3\}_2 \cdot \{CH_3O(CH_2CH_2O)_3CH_3\}$. (20)

4.12 g (23.12 mmol) of $CH_3O(CH_2CH_2O)_3CH_3$ (triglyme) is added dropwise to a stirred suspension of 10.50 g (23.12 mmol) of $Ca\{CF_3C(O)CHC(O)CF_3\}_2$ in 150 ml of toluene. Stirring is continued for 1 h. The slightly turbid reaction mixture is filtered and the clear filtrate is evaporated to dryness under reduced pressure at 40° C. The solid residue is stirred with 100 ml of pentane for 0.5 h and then filtered off. The colourless product is then dried in vacuo at room temperature for 4 h.

Yield: 10.90 g of 20 (74.6%).
Melting point: 120°-122° C.
$^1$H NMR in CDCl$_3$: $\delta(CH_3)$ 3.29 ppm (s) $\delta(CH_2CH_2)$ 3.53, 3.65 ppm (m) and 3.91 ppm (s) $\delta(CH)$ 5.94 ppm (s).
Elemental analysis: found (calculated) (%) C 34.22 (34.17); H 3.22 (3.16); F 35.61 (36.07).

Example 21

$Ca\{CF_3C(O)CHC(O)CH_3\}_2 \cdot \{CH_3O(CH_2CH_2O)_3CH_3\}$. (21)

0.18 g (1.00 mmol) of $CH_3O(CH_2CH_2O)_3CH_3$ (triglyme) is added dropwise to a stirred suspension of 0.35 g (1.00 mmol) of $Ca\{CF_3C(O)CHC(O)CH_3\}_2$ in 25 ml of toluene. Stirring is continued for 1 h. The slightly turbid reaction mixture is filtered and the clear filtrate is evaporated to dryness under reduced pressure at 40° C. The light yellow product solidifies on drying in vacuo at room temperature for 4 h.

Yield: 0.51 g of 21 (97.3%).
Melting point: 65°-67° C.
$^1$H NMR in $C_6D_6$: $\delta(OCH_3)$ 3.11 ppm (s) $\delta(CH_2CH_2)$ 3.11, 3.24 ppm (m) and 3.33 ppm (s) $\delta(CH_3)$ 1.86 ppm (s) $\delta(CH)$ 5.76 ppm (s).
Elemental analysis: found (calculated) (%) C 41.35 (41.22); H 5.03 (4.96).

Example 22

Sublimation of Ba-, Sr- and Ca-β-diketonate-ligand Complexes

Sublimation of various Ba-, Sr- and Ca-β-diketonate ligand complexes is performed at reduced pressure (0.5-0.01 Mm Hg) and temperatures of 85°-180° C. Results are presented in Table I.

Example 23

Co-evaporation of $Ba\{CF_3C(O)CHC(O)CF_3\}_2$ with $CH_3OCH_2CH_2OCH_3$ (Glyme, DME) as the Neutral Coordinating Ligand A dry $N_2$ flow (6 liters per hour) was led over $Ba\{CF_3C(O)CHC(O)CF_3\}_2$ (100 mg) at 225° C. for 3 hours and then led through a cold trap (−80° C.) in order to condense any transported Ba-compound. However, after the experiment, no barium could be detected in the cold trap. When, instead of a dry $N_2$ flow, a $N_2$ flow (6 liters per hour), saturated at 25° C. with $CH_3OCH_2CH_2OCH_3$ (dimethoxyethane), is led over $Ba\{CF_3C(O)CHC(O)CF_3\}_2$ (100 mg) at 225° C. for 3 hours, the condensate in the cold trap contains 5 mg of barium as $Ba\{CF_3C(O)CHC(O)CF_3\}_2 \cdot 2\{CH_3OCH_2CH_2OCH_3\}$ (1) dissolved in $CH_3OCH_2CH_2OCH_3$. In a similar experiment, performed with $Ba\{CF_3C(O)CHC(O)CF_3\}_2$ at a temperature of 145° C., after 2 hours the condensate contains about 1 mg of barium.

Example 24

Co-evaporation of Ba{CF₃CF₂CF₂C(O)CHC(O)C(CH₃)₃}₂ with CH₃OCH₂CH₂OCH₃ (glyme, DME) as the Coordinating Neutral Ligand

A dry $N_2$ flow (6 liters per hour) was led over Ba{CF₃CF₂CF₂C(O)CHC(O)C(CH₃)₃}₂ (100 mg) at 150° C. for 1 hour and 45 minutes and then led through a cold trap ($-80°$ C.) in order to condense any transported Ba-compound. After the experiment no barium could be detected in the cold trap. When however, instead of a dry $N_2$ flow, a $N_2$ flow (6 liters per hour), saturated at 25° C. with CH₃OCH₂CH₂OCH₃ (dimethoxyethane), is led over Ba{CF₃CF₂CF₂C(O)CHC(O)C(CH₃)₃}₂ (100 mg) at 150° C. for 2.5 hours, the condensate in the cold trap contains 0.1 mg of barium.

Example 25

MOCVD Deposition of BaF₂ from Ba{CF₃C(O)CHC(O)CF₃}₂ · {CH₃O(CH₂CH₂O)₄CH₃} (6)

In a hot-wall MOCVD apparatus, a dry $N_2$ flow (97 sccm) was led over Ba{CF₃C(O)CHC(O)CF₃}₂ · {CH₃O(CH₂CH₂O)₄CH₃} at temperatures ranging from 105° C. to 175° C., and mixed with $N_2$ (1150 sccm) and $O_2$ (415 sccm) before entering the reactor chamber. Deposition was performed on a polycrystalline substrate of yttria-stabilized zirconia (YSZ) at 800° C.; pressure 10–20 torr. X-ray diffraction analysis (XRD) after deposition proved the deposit to be BaF₂. Growth rates varied from 1.3 ug/cm²/min (T evaporator 105° C.) to 65 ug/cm²/min (T evaporator 175° C.).

Example 26

MOCVD Deposition of SrF₂ from Sr{CF₃C(O)CHC(O)CF₃}₂ · {CH₃O(CH₂CH₂O)₄CH₃} (18)

In a hot-wall MOCVD apparatus, a dry $N_2$ flow (100 sccm) was led over Sr{CF₃C(O)CHC(O)CF₃}₂ · {CH₃O(CH₂CH₂O)₄CH₃} at 146° C., and mixed with $N_2$ (733 sccm) and $O_2$ (833 sccm) before entering the reactor chamber. Deposition was performed on YSZ at 800° C.; pressure 15 torr. XRD after deposition proved the deposit to be SrF₂. The growth rate was 30 ug/cm²/min.

Example 27

MOCVD deposition of CaF₂ from Ca{CF₃C(O)CHC(O)CF₃}₂ · {CH₃O(CH₂CH₂O)₃CH₃} (20)

In a hot-wall MOCVD apparatus, a dry $N_2$ flow (100 sccm) was led over Ca{CF₃C(O)CHC(O)CF₃}₂ · {CH₃O(CH₂CH₂O)₃CH₃} at 146° C., and mixed with $N_2$ (733 sccm) and $O_2$ (833 sccm) before entering the reactor chamber. Deposition was performed on YSZ at 800° C.; pressure 15 torr. XRD after deposition proved the deposit to be CaF₂. The growth rate was 18 ug/cm²/min.

Example 28

MOCVD Deposition of YBa₂Cu₃O₇₋ₓ from Y{(CH₃)₃CC(O)CHC(O)C(CH₃)₃}₂, Ba{CF₃C(O)CHC(O)CF₃}₂ · {CH₃O(CH₂CH₂O)₄CH₃} (6) and Cu{(CH₃)₃CC(O)CHC(O)C(CH₃)₃}₂

In a hot-wall MOCVD apparatus, three dry $N_2$ flows (each 97 sccm) were led over Y{(CH₃)₃CC(O)CHC(O)C(CH₃)₃}₃, Ba{CF₃C(O)CHC(O)CF₃}₂ · {CH₃O(CH₂CH₂O)₄CH₃} and Cu{(CH₃)₃CC(O)CHC(O)C(CH₃)₃}₂, at a temperature of resp. 163.3° C., 147.2° C. and 147.2° C. for the Y, Ba and Cu compound. These flows were mixed before entering the reactor chamber together with flows of $N_2$ (1825 sccm) and $O_2$ (2100 sccm). The latter gas stream had been led beforehand through a water vaporiser (T water 50° C.). Depositions were performed on single-crystal MgO substrates at 800° C. and 900° C.; total gas pressure 12 torr. XRD after deposition proved the deposits to contain YBa₂Cu₃O₇₋ₓ, oriented along the c-axis.

Example 29

MOCVD Deposition of BaO from Ba{CF₃C(O)CHC(O)CF₃}₂ · {CH₃O(CH₂CH₂O)₄CH₃} (6)

In a hot-wall MOCVD apparatus, a dry $N_2$ flow (97 sccm) was led over Ba{CF₃C(O)CHC(O)CF₃}₂ · {CH₃O(CH₂CH₂O)₄CH₃} at 164.5° C., and mixed with $N_2$ (2008 sccm) and $O_2$ (2100 sccm) before entering the reactor chamber. The latter gas stream had been led beforehand through a water vaporiser (T water 20.5°C.). Deposition was performed on a single-crystal MgO with (100) orientation at 893° C.; pressure 42 torr. XRD after deposition proved the deposit to contain BaO. No fluor was detected by X-ray Photoelectron Spectroscopy (XPS). The growth rate was 8 ug/cm²/min.

Example 30

MOCVD Deposition of SrO from Sr{CF₃C(O)CHC(O)CF₃}₂ · {CH₃O(CH₂CH₂O)₄CH₃} (18).

In a hot-wall MOCVD apparatus, a dry $N_2$ flow (100 sccm) was led over Sr{CF₃C(O)CHC(O)CF₃}₂ · {CH₃O(CH₂CH₂O)₄CH₃} at 138.1° C., and mixed with $N_2$ (733 sccm) and $O_2$ (833 sccm) before entering the reactor chamber. The latter gas stream had been led beforehand through a water vaporiser (T water 50.2° C.). Deposition was performed on polycrystalline YSZ at 801.4° C.; pressure 25 torr. XRD after deposition proved the deposit to contain SrO. The growth rate was 11 ug/cm²/min.

Example 31

MOCVD Deposition of CaO from Ca{CF₃C(O)CHC(O)CF₃}₂ · {CH₃O(CH₂CH₂O)₃CH₃} (20)

In a hot-wall MOCVD apparatus, a dry $N_2$ flow (100 sccm) was led over Ca{CF₃C(O)CHC(O)CF₃}₂ · {CH₃O(CH₂CH₂O)₃CH₃} at 139.1° C., and mixed with $N_2$ (733 sccm) and $O_2$ (833 sccm) before entering the reactor chamber. The latter gas stream had been led beforehand through a water vaporiser (T water 50.2° C.). Deposition was performed on polycrystalline YSZ at 800.3° C.; pressure 25 torr. XRD after deposition proved the deposit to contain CaO. The growth rate was 10 ug/cm²/min.

TABLE I

Volatility of some compounds according to the invention and of some corresponding barium-, strontium- and calcium-β-diketonates upon sublimation in vacuo. The numbers refer to the numbers of the structure formulas in the opening description.

| Compound (100 mg) | P (mm Hg) | T (°C.) | Sublimed (% after 1 hour) |
|---|---|---|---|
| Ba{CF₃C(O)CHC(O)CF₃}₂ | 0.5 | 150 | 0 |
| 1 | 0.5 | 150 | 5 |
| 2 | 0.02 | 160 | 5 |
| 3 | 0.03 | 125 | 13 |
| 4 | 0.02 | 165 | 40 |
| 5 | 0.03 | 145 | 60 |
| 6 | 0.03 | 150 | 95 |
| 7 | 0.03 | 165 | 95 |
| 8 | 0.02 | 145 | 95 |
| 9 | 0.01 | 180 | 48 |
| 10 | 0.01 | 170 | 18 |
| 11 | 0.02 | 170 | 11 |
| 12 | 0.02 | 145 | 95 |
| Ba{CF₃C(O)CHC(O)CH₃}₂ | 0.02 | 150 | 0 |
| 13 | 0.03 | 145 | 13 |
| 14 | 0.02 | 170 | 16 |
| Ba{CF₃CF₂CF₂C(O)CHC(O)C(CH₃)₃}₂ | 0.02 | 150 | 0 |
| 15 | 0.02 | 155 | 80 |
| 16 | 0.02 | 150 | 80 |
| Sr{CF₃C(O)CHC(O)CF₃}₂ | 0.06 | 95 | 0 |
| 17 | 0.06 | 95 | 25 |
| 18 | 0.01 | 115 | 95 |
| Ca{CF₃C(O)CHC(O)CF₃}₂ | 0.05 | 85 | 0 |
| 19 | 0.05 | 85 | 50 |
| 20 | 0.02 | 100 | 95 |
| Ca{CF₃C(O)CHC(O)CH₃}₂ | 0.02 | 135 | 0 |
| 21 | 0.02 | 135 | 11 |

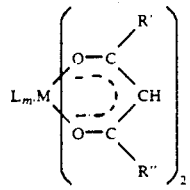

We claim:

1. Volatile organic barium, strontium and calcium compounds, comprising a complex of a barium-, strontium- or calcium-β-diketonate and one or more coordinating ligands, characterized in that at least one coordinating ligand of the barium, strontium or calcium compound is formed by a neutral oxygen donor ligand.

2. Organic barium, strontium and calcium compounds according to claim 1, characterized in that the neutral oxygen donor ligand is an acyclic ether, a cyclic ether or a glycol ether.

3. Organic barium, strontium and calcium compounds according to claim 2, characterized in that the cyclic ether is (CH₂CH₂O)₆, and the glycol ether is CH₃O(CH₂CH₂O)$_n$CH₃ or HO(CH₂CH₂O)$_n$CH₃ in which n is 1, 2, 3, 4, 5 or 6.

4. Organic barium, strontium and calcium compounds according to one of the claims 1-3, characterized in that the side chains R', R" of the β-diketonate R'C(O)CHC(O)R" are alkyl groups containing 1-4 carbon atoms or substituted alkyl groups containing 1-3 carbon atoms.

5. Organic barium, strontium and calcium compounds according to claim 4, characterized in that a substituted alkyl group contains or more fluorine atoms.

6. Organic barium, strontium and calcium compounds according to claim 5, characterized in that a substituted alkyl group is either CF₃ or n—C₃F₇.

* * * * *